United States Patent [19]

Saxholm

[11] 4,140,582
[45] * Feb. 20, 1979

[54] SUPPORTING ELEMENT FOR USE IN MICROBIOLOGICAL, SEROLOGICAL, IMMUNOLOGICAL CLINICAL-CHEMICAL AND SIMILAR LABORATORY WORK

[76] Inventor: Rolf Saxholm, Aastadveien 2, 1362 Billingstad, Norway

[*] Notice: The portion of the term of this patent subsequent to Oct. 12, 1993, has been disclaimed.

[21] Appl. No.: 731,103

[22] Filed: Oct. 8, 1976

Related U.S. Application Data

[60] Continuation of Ser. No. 602,745, Aug. 7, 1975, Pat. No. 3,985,608, which is a division of Ser. No. 33,594, May 1, 1970, Pat. No. 3,791,930.

[30] Foreign Application Priority Data

May 3, 1969 [NO] Norway .............................. 1832/69

[51] Int. Cl.² .............................................. C12K 1/10
[52] U.S. Cl. .............................. 195/127; 195/103.5 K
[58] Field of Search ................. 195/103.5 R, 103.5 K, 195/103.5 M, 127

[56] References Cited

U.S. PATENT DOCUMENTS 3,791,930   2/1974   Saxholm ..................... 195/103.5 R
3,985,608  10/1976   Saxholm ......................... 195/127

Primary Examiner—Raymond N. Jones
Assistant Examiner—Robert J. Warden
Attorney, Agent, or Firm—Haseltine, Lake & Waters

[57] ABSTRACT

For microbiological and other laboratory work in which supporting elements carrying an active substance is brought into contact with a substrate there is provided a supporting element of tubular or other shape and adapted to be forced through the substrate to the bottom of the same and thereby wholly or partly to confine an area of the substrate. The element carries the active substance on the side facing the confined area and isolates it from the substrate on the opposite side. The supporting element may comprise magnetic material and be pulled to the bottom of the substrate by magnetic force.

4 Claims, 15 Drawing Figures

SUPPORTING ELEMENT FOR USE IN MICROBIOLOGICAL, SEROLOGICAL, IMMUNOLOGICAL CLINICAL-CHEMICAL AND SIMILAR LABORATORY WORK

CROSS-RELATED APPLICATION

This application is a continuation of co-pending application Ser. No. 602,745 filed Aug. 7, 1975 now issued as U.S. Pat. No. 3,985,608 which, in turn, is a division of application Ser. No. 33,594 filed May 1, 1970 and issued as U.S. Pat. No. 3,791,930.

BACKGROUND OF THE INVENTION

This invention relates to a new technique permitting rationalization and automation of microbiological, serological, immunological, clinical-chemical and similar laboratory work.

Before the invention is explained, it will be expedient to give some general background information.

Bacteria are grown in substrates (media) which are either liquid (broth) or of more or less solid consistency. Growth in liquid substrates takes place throughout the entire substrate, while in solid substrates the growth usually takes place on the surface.

The solid substrates are made from the liquid by adding agar (or some other substance, such as gelatine) in various concentrations, or through the cogulation of albumin. There are a number of different types of liquid and solid substrates. Often they have a common basic composition, but otherwise the composition changes according to which substances are required for the growth of the bacteria in question.

Many, though not all, bacteria decompose and utilize matter in different ways. This can be registered by various chemical or physico-chemical reactions. As an example may be mentioned the fermentation or splitting of various types of so-called "sugar" (hereinafter called sugar) by bacteria. This formentation, considered for the whole series of sugar types in question, is often characteristic of the individual type of bacterium, and frequently differs from one bacterium to the other. This circumstance is widely exploited as an aid in distinguishing bacteria from one another.

When a bacterium decomposes a sugar to acid products, the pH value in the substrate decreases, as may be observed by a change in the color of an added indicator. If, for example, a sugar is added to a solid substrate as a fermentation basis, and bromothymol blue is added as an indicator, the result of inoculation with bacteria that break down sugar, and with bacteria that do not, is as follows: The sugar-splitting bacteria will grow on the surface of the substrate and form yellow colonies, while the non-splitting bacteria will form colonies of the same blue color as that of the substrate before inoculation. Yellow and blue colonies may lie close together, side by side, on the surface of the substrate.

A corresponding liquid substrate will change its color to yellow if sugar-splitting bacteria grow in it, and will remain blue if the growth is purely of non-splitting bacteria.

When, as an aid to classification, fermentation determinations are carried out, liquid substrates are usually employed.

Since one of the objects of the invention is to rationalize fermentation tests — without limiting its scope to this field — a more detailed description will be given of how a fermentation test is carried out according to a known method.

A pure culture of the micro-organism to be classified by the fermentation test must be prepared. Samples from this pure culture are inoculated into broths which have already been poured into test tubes. These broths contain an indicator and various types of sugar. The test tubes are enclosed with plugs or caps. The test tubes containing the broths are placed in racks and incubated for growth and reaction. The result is read by inspecting each tube, and is noted by hand.

This method requires that the test tubes be placed in the racks by hand. Each tube of broth contains only one kind of sugar, but the number of kinds of sugar, and thus of tubes, may often be comparatively high. This means that handling the tubes and segregating them according to type of sugar when they are to be arranged in rows in the racks, can be a relatively laborious process. Furthermore, there is room for confusion and error.

The inoculation process is also relatively laborious. The inoculation of each test tube containing the sugar broth involves removal of the stopper, the upper edge of the tube being sterilized by a flame to remove any possible microbial contamination, and the stopper being replaced.

The test tubes, which are often of glass, must, after having been read, go through a time-consuming and laborious process before they can be used anew. First they are put in an autoclave to kill the cultures. Then they are empited, washed, and rinsed, whereupon they are fitted with stoppers. After this they are sterilized and are once again ready to receive new charges of broths containing various types of sugar and indicator.

The preparation of the substrates to be put into the test tubes also demands time and labor. First, the broth must be prepared and then, to portions of this, a number of different types of sugar have to be added. These mixtures are then poured into test and duly sterilized. The tubes are marked to indicate the type of sugar therein. They are then placed in a refrigerator, ready for use.

The test tubes require a good deal of space on account of their relatively large size and number. This makes itselt felt in the laboratory work, during storing in the refrigerator and incubator, storing and transport from producer to user. In addition, the racks require storing and cleaning.

The fermentation test described above can also be carried out by positioning prefabricated bodies carrying the various types of sugar in a known solid substrate in a dish or container. The indicator may be conveniently present in the sugar bodies, or, alternatively, it may, in known manner, have been added to the substrate in advance.

Before the bodies are positioned, the substrate surface in the dish is evenly inoculated all over with a suspension or broth containing a pure culture of the micro-organism.

After the bodies have been introduced onto the surface of the substrate, the sugar — and the indicator if this has been added to the bodies — will diffuse out into the substrate. This takes place relatively fast in the substrates normally used. As a result, a successful reaction will not occur if the sugar is applied via a paper disc into which it has been absorbed, or via a tablet into which the sugar has been mixed. The diffusion must be delayed or limited.

SUMMARY OF THE INVENTION

According to the invention, the substrate around the applied body is limited, so that the sugar diffusing out will remain inside a peripherally closed chamber or confined region and equalize itself there with an evenly distributed concentration. Thus, this final concentration is dependent upon the volume of substrate enclosed and upon the quantity of the sugar applied.

A more detailed description according to the invention, will be given hereafter. The limitation is achieved by means of supporting elements which encompass or confine a space closed laterally on all sides. The supporting elements are pressed down into the solid or semi-solid substrate, preferably so that their lower edges reach the bottom of the dish, while their upper edges preferably protrude somewhat above the surface of the substrate. In other words, the supporting element should preferably be somewhat higher than the depth of the substrate, which is generally about 0.5 cm or less. The diameter can be, for example, 0.5-1.5 cm or some other suitable size. The supporting elements may be open or closed at the top.

The supporting elements contain those types of sugar which are to take part in the reactions. Suitable concentrations and quantities of the sugars, for example, absorbed in filter paper or mixed into a suitable mass, are placed, during manufacture, in an expedient manner in the supporting elements. This can be achieved, for example, by means of a lining containing the sugar types and fixed to the inside of the walls of the supporting element. This lining may, if desired, rest on a lower inner shelf or step just above the lower edge of the supporting element. Alernatively, the sugars can be placed in hollows in the walls of the supporting element, in which case internal lamellae are perforated so that diffusion can take place into the space actually enclosed by the supporting element. The bottom of the wall cavity may conveniently consist of the solid lower edge portion of the supporting element.

In addition to the walls which surround the supporting element to carry the types of sugar, internal installations in the supporting element may be used for the same purpose. Thus, in the center of the supporting element, there may be mounted a torpedo-, projectille- or star-shaped part, or other similar parts of expedient shape. They can be fixed, for example, by means of a supporting spider carried by the upper edge of the supporting element. Furthermore, the supporting element can have partition wall sections of various shapes which fully or partly subdivide the space which the supporting element actually surrounds. These partition walls, and in fact all internal installations, may, like the surrounding walls, be of hollow construction with perforated wall lamellae.

After a supporting element containing a sugar has been placed in the substrate, diffusion takes place in the part of the substrate enclosed by the walls of the supporting element. In the case of supporting elements with perforated internal wall lamellae, diffusion takes place through these holes.

The amount of sugar which in one or another of the methods mentioned is introduced together with the supporting elements during the production process, is so adjusted that after diffusion into the substrate bordered by the walls of the supporting element, the sugar will assume a concentration suitable for the fermentation tests to be carried out.

When carrying out fermentation tests, good results will be achieved irrespective of the geometrical form of the cross-section of the supporting element, but even though this is so, it may be of interest to discuss the shape of the supporting element in relation to diffusion equilibrium. The shape of the supporting element and the positioning of the sugar affects the rapidity with which the final concentration of the sugar is established in the substrate in the supporting element. A circular supporting element, with the sugar placed along the wall, surrounds a quantity of substrate which will be relatively slowly penetrated compared to non-circular shapes due to the fact that a circle has a relatively large area compared to its circumference. Placing the sugar in the middle of the round supporting element and/or along partition walls in addition to along the inner wall of the supporting element entails a more rapid state of diffusion equilibrium. Also, for example, a narrow rectangular supporting element, with the sugar placed along the walls, will be favorable for a relatively rapid establishment of the final sugar concentration in the substrate enclosed. With certain reactions other than fermentation tests, the choice of an expedient shape of supporting element may have practical consequences for the course and outcome of the reaction.

An actual or "positive" fermentation reaction is revealed by change of indicator color after incubation at 37° C. for a suitable period, while no or "negative" reaction is characterized by no change of color. The results of reaction are easy to read.

In a container containing a substrate, for example, a Petri dish, a number of supporting elements are placed at suitable mutual distances. Each supporting element contains one type of sugar, and thus all the supporting elements together represent the different types of sugar with which the fermentation test with the bacterium culture in question is to be made.

It is convenient to supply the supporting elements to the substrate from a dispenser similar to those normally used for positioning paper discs containing antibiotics. The supporting elements containing the sugars are stored under sterile conditions, stacked up on top of one another in magazines, each magazine containing supporting elements having the same kind of sugar. In the dispenser or depositing device there is room for several magazines side by side, each magazine containing a different type of sugar.

Especially if delicate substances are contained in the supporting elements, it may be preferable to store them not only under sterile conditions in magazines, but also vacuum-packed After the supporting elements have been positioned on the surface of the solid substrate they may, by hand or machine, be pressed so that they penetrate the substrate and establish contact with the bottom of the dish, with the help of, for example, a plunger or similar device which presses down all the supporting elements in one and the same operation. The upper edge of the supporting elements, according to the invention, should preferably protrude somewhat above the surface of the substrate, so there is usually no danger of the surface of a plunger contacting the substrate.

If required, the supporting elements may be provided, at their lower edges, with small anchoring feet in order to prevent rebound from the surface of the substrate.

The supporting elements may be mounted in a supporting skeleton by means of which they can be simultaneously pressed to penetrate the substrate.

In accordance with the invention in patent application Ser. No. 705,539, the supporting elements may be made to respond to magnetic forces or, in other words, they may be made magnetically responsive. By magnetic forces, they are attracted to penetrate the substrate and to make contact with the bottom of the dish. If required, the magnetic force may be applied after the supporting elements, by gravity, have landed on the surface of the substrate. The magnetizable parts can be placed, for example, inside the wall of the supporting element at its lower part or edge, and around the entire circumference. Alternatively, for example, the entire wall of the supporting element may be ferromagnetic. This material may conveniently have the form of an unbroken iron ring or sleeve, or also of granular parts, the maximum size being determined by the thickness of the tubular wall.

Below and along the upper, outer edge of the supporting elements, they may be provided with a collar of iron of suitable size and shape in order to increase the response of the supporting element to the magnetic field. If required, the collar may carry slim, downwardly projecting supporting studs extending outside the element and terminating flush with the bottom thereof. Their number may, for example, be four, and they may expediently be placed opposite one another so as to offer a balanced support.

It may be convenient to make the lower edge of the supporting element fairly sharp or bevelled so as to facilitate penetration of the supporting element through the substrate.

The supporting elements are discarded after use. Except for the above mentioned magnetizable components, they can, with advantage, be made of plastic or the like, which is destroyed by burning.

The sugar fermentation reactions are not critically dependent upon complete contact or sealing between the bottom of the dish and the lower edge of the supporting element.

Even a roughly cut lower edge of a supporting element ensures reactions of just as good quality as those with very good contact. Nevertheless it is possible, if desired, to establish adhesion between the lower edge and the bottom of the dish.

The identities of the reaction are determined automatically or semi-automatically in accordance with the invention described in patent application Ser. No. 705,539 by means of defined positions.

Also the outcome of each reaction is a function which may be read by meachine in accordance with the said patent application Ser. No. 705,539. The readings are made as indicated in the patent application, preferably under visual control. The data machine used indicates in a simple manner whether a reaction is positive or negative, or the degree of positivity shown by the reactions. In such a case as this, with clear, distinct color reactions and well defined criteria for determining the outcome of a reaction, it may, in accordance with the above mentioned patent application, be possible to take the readings fully automatically.

Conventionally, when carrying out fermentation tests, one investigation is made for each type of sugar. A defined, convenient concentration of the sugar is used. Investigations carried out by the Inventor indicate that it would be possible to achieve a better differentiated diagnostic expression if several concentrations of the particular sugar were used in the test. Such a method would be prohibitive with the working methods available by present day techniques. Even when only one concentration of each kind of sugar is used, fermentation tests impose a heavy load on the laboratories.

The invention, however, makes it possible in a simple and labor-saving way to carry out a fermentation test with several concentrations of one kind of sugar. Apart from using a separate supporting element for each sugar concentration, it is possible to use one supporting element for all concentrations, the supporting element being divided into separate chambers to carry the sugar concentrations. The supporting element may in such a case, for example, have the shape of a relatively long rectangular structure divided into consecutive transverse rectangular sections. Each section contains a given concentration of the sugar in such a way that there is a successive increase or decrease in the sugar concentration from section to section in the long rectangular supporting element. This supporting element represents threrefore a particular type of sugar, and its sections, various concentrations of that sugar.

The type of sugar is identified by the position of the rectangular supporting element as such, and the concentration of sugar where a possible fermentation first occurs is determined by the position of the chamber concerned in the section row.

The supporting element under discussion may also be used with different types of sugar in the chambers.

However, as mentioned above, the invention is not restricted to use in fermentation tests, but is applicable to a large number of microbiological, serological, immunological, clinical-chemical and similar tests.

For example, the invention could be applicable to sensitivity determinations of bacteria towards antibiotics (and chemotherapeutics).

Today such determinations are usually made by means of discs containing antibiotics. A mechanical and automactic embodiment of this method is described in patent application No. 705,539. The principle of the antibiotic disc method is to measure the diameter of the inhibition zone around the antibiotic disc and use this measurement as an expression of the sensitivity of the bacterium towards the antibiotic concerned, of which the disc contains a given amount.

In contrast to this, the present invention perments sensitivity determinations to be carried out in a simple manner by means of a titration technique. In this manner, a quantitative determination is achieved in terms of different concentrations of an antibiotic. In some cases this is more advantageous than the conventional method involving measuring the size of the zone diameter. The methods supplement one another.

According to the invention, supporting the elements containing various concentrations of any antibiotic may be manufactured in advance for use in connection with the quantitative technique discussed above. In a titration test a given series of supporting elements is used for each antibiotic in such a way that the concentration of the antibiotic in question increases from one supporting element to the next. In addition to individual supporting elements, a supporting element subdivided into section chambers, as described above, can also be used for this purpose. The chambers have been supplied in advance with various concentrations of an antibiotic increasing in steps from chamber to chamber. Observations are made of the lowest concentration which inhibits growth, assuming that the bacterium being investigated is sensitive towards the antibiotic in question.

Today, if it is desired to carry out a quantitative sensitivity examination of the kind mentioned, this must be done in a series of test tubes containing broth, or in containers holding solid substrate, containing concentrations of antibiotic increasing in steps. On account of the labor this involves, this present-day technique would be prohibitive as a general routine method. Yet, in spite of the amount of work involved, it is used when determining the sensitivity of tubercle bacilli.

The reason why sensitivity determinations of tubercle bacilli towards antibiotics differ from the sensitivity determinations of other bacteria, is the relatively very slow growth rate of tubercle bacilli. One consequence of this fact is that it is not convenient to determine the sensitivity of tubercle bacilli by the antibiotic disc method in the conventional manner.

However, the present invention makes it possible to determine the sensitivity of tubercle bacilli also by measuring the size of the zone inhibited. This can be achieved by using a relatively long and narrow rectangular supporting element as a support for an antibiotic. This antibiotic is fixed to the inside of one of the short sides of the supporting element. The diffusion of the antibiotic concerned is guided by the shape of the supporting element in a compressed volume along the longitudinal axis of the rectangular supporting element. The length of the zone inhibited is a measure of the sensitivity. The supporting elements may be open or closed at the top, the closure, when present, being in the form of a flat transparent roof. This cover will delay the desiccation of the substrate and reduce the risk of contamination during the incubation period of several weeks at 37° C. which is necessary for permitting the growth of the tubercle bacilli to develop. In itself, the sealing of the substrate dish is not entirely sufficient to afford protection against a certain degree of desiccation during such a long period of incubation. Additional sealing of the dishes is required (for example with tape) or they can be incubated inside plastic bags or boxes. These measures can be rendered unnecessary by using supporting elements closed at the top as mentioned above.

This invention also lends itself to an expedient application of a serological technique, particularly an immunodiffusion or precipitation technique. This very important technique has a multifarious and increasing application, but it is laborious and difficult to use in series tests. With the help of this invention, this technique will be made available in a great many fields for routine laboratory work and will, to a significant degree, contribute to increasing the breadth of information conerning laboratory investigation and research and to enhance their significance.

Instead of inoculating the substrate (preferably at the surface) with a bacterium culture, it is possible, in this case, to spread a quantity of antigen or antibody over the surface of the substrate, or mix it in with the substrate before pouring it into the dishes, all according to whether the supporting elements contain antibody or antigen respectively. When employing a quantitative precipitation technique, the prefabricated supporting elements contain graded quantitites of the said substances.

It is only necessary for the substrate to be a nutrient when microbial growth is to take place. In addition to the compositions referred to earlier, it may be made on the basis of cellulose, starch or other suitable substances. Generally speaking the composition shall consist of a material which permits diffusion and gives it a solid or semi-solid consistency. The latter is usually somewhat elastic, but it may also be plastic. Furthermore, the substrate must be penetrable by the supporting elements.

In some cases, it may be sufficient to use supporting elements that are partially open laterally, for example, rectangular supporting elements from which the one short wall is missing, or which form open curves. Supporting elements of such a shape will constitute something between the fully open ones, known per se, for example, paper discs, and those described above which surround a space closed on all sides. The material which is to diffuse is fixed to the far wall of the supporting element, and the diffusion, in its first phase, is guided in a fixed direction by the walls of the supporting element. When the diffusion has extended beyond the bounds of the supporting element, it will spread in all directions.

The supporting elements may be of various shapes, each suited for specific diffusion experiments. This may apply to different immunodiffusion tests but is not limited to this particular application. Thus, it may be very useful to consider and make use of the same expedient when bacterial growth is involved in the experiments, for example, when testing synergism or antagonism between antibiotics towards bacteria. This investigation is an important supplement to the usual sensitivity determinations, and the possibility now available to include such tests in normal routine investigations is a large and important step forward.

The invention may also be used in connection with investigations involving growth factors. In advance, growth-promoting substances can be placed in the peripherally, for example fully, closed supporting elements. After placing the supporting elements in the inoculated substrate there will, through diffusion of the substances mentioned into the basic substrate in the dish, be produced new substrates in the various supporting elements, different from that originally present in them. These new substrates consist of the basic substrate and one or more additional different components all dependent on the number of growth-promoting substances placed in the supporting elements. Different substrates are thus produced in one dish. Observations are then made of the inoculated bacterium culture in the different supporting elements to see whether they react with abundant, unchanged or possibly reduced growth, in response to the addition of the various substances. The technique may be used in connection with diagnosis or for purely experimental purposes.

Some test methods require a secondary application, to the reaction region, of a particular substance (or substances) after a suitable period (or periods) in the course of the reaction, for example, after incubation for growth has taken place. Such a technique may be carried out by means of the invention. By using a dispenser, the secondary application can be made in the same pattern as the one used for the first positioning. For example, paper discs or other suitable bodies containing the substance or substances to be added, may be placed in the supporting elements. Another way of making secondary applications is to use a device having a number of inoculation points or pipettes arranged in the same pattern as that in which the supporting elements were placed.

This technique, characterized by the secondary application of substances after suitable periods of time have elaped, may also be useful in the case of a quantitative method utilizing supporting elements which contain a substance present in a graded series of concentrations from one supporting element to the next. The possibility is thereby opened of adapting the method to different, relatively complicated titration techniques which today are carried out with liquid substances in test tubes. This also applies, for example, to reactions such as those in which red blood corpuscles are used to bring about haemolysis or haemagglutination as an aid to determining the titration end-points. Secondarily, the red corpuscles may be placed on the surface of the substrate within the supporting elements, or they may have been admixed with the substrate in advance. The substrate may have a very simple composition. It may, for example, be relatively low. The substrate may also contain substances other than the red corpuscles mentioned above, which take part in the reactions in constant quantities from reaction to reaction.

Alternatively, titration techniques may be employed by using the substances secondarily applied in graded concentrations, while the substances contained in the supporting elements in this case form a series with a constant concentration level.

Each supporting element need not contain only one substance, but may contain several. These substances may be pooled, or positioned separately at different and isolated places in the supporting element, in order to prevent a reaction from taking place between the substances before diffusion into the substrate.

The supporting elements may also be produced without substances being added during the manufacturing process, but with the possibility of adding required materials after the supporting elements have been placed in position in the substrate. With this object in view, the supporting elements may, for example, be supplied with a funnel-shaped input channel leading to a cavity in the wall of the supporting element where, in advance, a piece of absorbent paper may have been placed. These supporting elements too, may be of various shapes, each of a design suited for various specific diffusion experiments, for example, for examining precipitation patterns, testing synergism or antagonism between antibiotics, or when examining growth factors. They may enclose a hollow space peripherally closed on all sides, or they may be partly open. The purpose is to give research workers a technical aid that can improve possibilities and facilitate their work in the wide field of experiment covered by diffusion techniques and microbiology.

Furthermore, the invention makes it easy to determine the level of concentration of antibiotics in tissue liquids and to carry out other assays.

The invention may be used in a quantitative and automatic technique based on spectrophotometric readings through the contents within the positioned supporting elements. This may apply, for example, to clinical-chemical tests. The system may be used for carrying out autoanalyzer work. Depending on how many supporting elements are positioned by the dispenser at a time, the invention may easily be used in connection with a 12-channel run or more. The invention may, for example, be used for screening tests.

The system of the invention is very flexible in use. It may be used both with substances which disperse rapidly, and with those which diffuse slowly in the substrate selected. This opens great possibilities for many different reactions and types of reaction to be adapted to the technique thus providing the inherent advantages which will be discussed in more detail below.

The system of the invention utilizes principles which were defined and explained in patent application Ser. No. 705,539. The advantages discussed in the said application will also benefit the present invention. They are concerned with the automation of laboratory work and primary noting of data taking into consideration a technically desirable, or even necessary human and visual guidance and control. They are further concerned with the possibility of establishing direct contact with an electronic data processing unit with the enormous advantages offered thereby. Due to the present invention, these principles may find a more general and comprehensive application and will benefit a wide range of various microbiological, serological, immunological, clinical-chemical and similar tests and research in diffusion techniques in biological and chemical fields.

A technique adapted to the invention will benefit by advantages in addition to those mentioned above. These advantages relate partly to the actual laboratory work itself, partly to the preparation of the substrate, to cleaning, partly to questions of storage and transport and finally to safety aspects in the laboratory work concerned, in that the risks of errors and confusion are greatly reduced.

A more detailed explanation of these conditions will be given with reference to the technique used in the bacterial fermentation of sugars, mentioned above. The invention involves only one inoculation for the entire series of sugars, as opposed to the system in use today, which requires one inoculation for each type of sugar, or, in some cases, for two or three types. Furthermore, there is only one cover, namely the lid of the Petri dish, to take off and replace, as compared with the present practice of using a plug or cap for each broth test tube corresponding to the individual sugar types inoculated. In addition, all the fermentation reactions are collected in one handy, convenient and space-saving unit, the Petri dish, as compared with the present somewhat untidy, laborous and cumbersome system with all the individual broth test tubes to be handled and spread out one after the other in the holes of a rack. A further disadvantage in this connection is that the individual test tubes containing the various types of sugar are alike and can only be distinguished by means of a label indicating the type of sugar contained. Relatively speaking, the number of substrate dishes to be handled is small, and they are all of the same type, whereas the broth-containing test tubes are many, all externally the same, yet containing various types of sugar.

Although the reading and noting by the new technique may be carried out automatically under visual control or fully automatically according to patent application Ser. No. 705,539, these operations are very laborious and time-consuming when conventional techniques are used, in which the various fermentation tubes, standing in close rows and columns in a rack arranged according to the kind of test and the type of sugar, have to be removed manually one by one for taking readings of the outcome and observing the identity, whereafter the data are noted by hand.

With the conventional technique, the risk of error is relatively large. This applies to the reading and noting of data. It also applies to the inoculation. This is repeated for every broth test tube in the series. It is possible to overlook a tube, or it may be inoculated from a loop which does not contain sufficient inoculate to promote growth. This leads to erroneous results.

Errors and confusion may also occur at an earlier stage. They may occur when the technical assistant fetches the test tubes containing the sugar broths. These are kept in a refrigerator and are grouped separately for each type of sugar. It may however happen that the test tubes that have not been used are put back in the refrigerator in a wrong group, inasmuch as the tubes in all groups have a similar outer appearance. Each test tube must therefore be checked.

Furthermore, errors and confusion may arise in the substrate department when the broths containing the various types of sugar are being prepared. Mistakes may also be made in affixing labels and when the tubes are transported to the refrigerator.

The fact already mentioned that a relatively large number of broths containing different sugars are required for fermentation tests, increases the possibility of error. This applies particularly when there are several specimens to be examined. In contrast to this, the technique according to the invention means that only a relatively small number of Petri dishes have to be handled, and all of the same type.

The invention will result in a considerable saving in space both during storage in the laboratory and during internal and external transport and dispatch. The small supporting elements can be housed in magazines as compact units as compared to the collection of relatively very large individual test tubes, which are awkward to handle. These require stands which take up a lot of space and have to be kept clean and free from contamination. Often the tubes are of glass, and must, after use, be put in an autoclave, washed and sterilized before they can be used again.

On the other hand, it is very simple, after use, to remove and destroy the Petri dishes and with them the supporting elements placed in the substrate. When removing them, it is of considerable advantage to be able to handle the small units, requiring little space, which the invention makes possible.

It is also very advantageous that the invention makes it possible to use a very simple and standardized substrate for various tests and experiments.

Although other modifications or versions of the fermentation test exist, none of them — or other laboratory methods currently in use or known — have any relation to the principles or system of the invention.

In the following, the invention will be described in more detail with reference to the drawings.

DETAILED DESCRIPTION

The supporting element according to the invention may be used for many tests and experiments, but in the following description there is primarily given an account of the determination of bacteria on the basis of their fermenting effect on various types of sugar.

Figure 1:
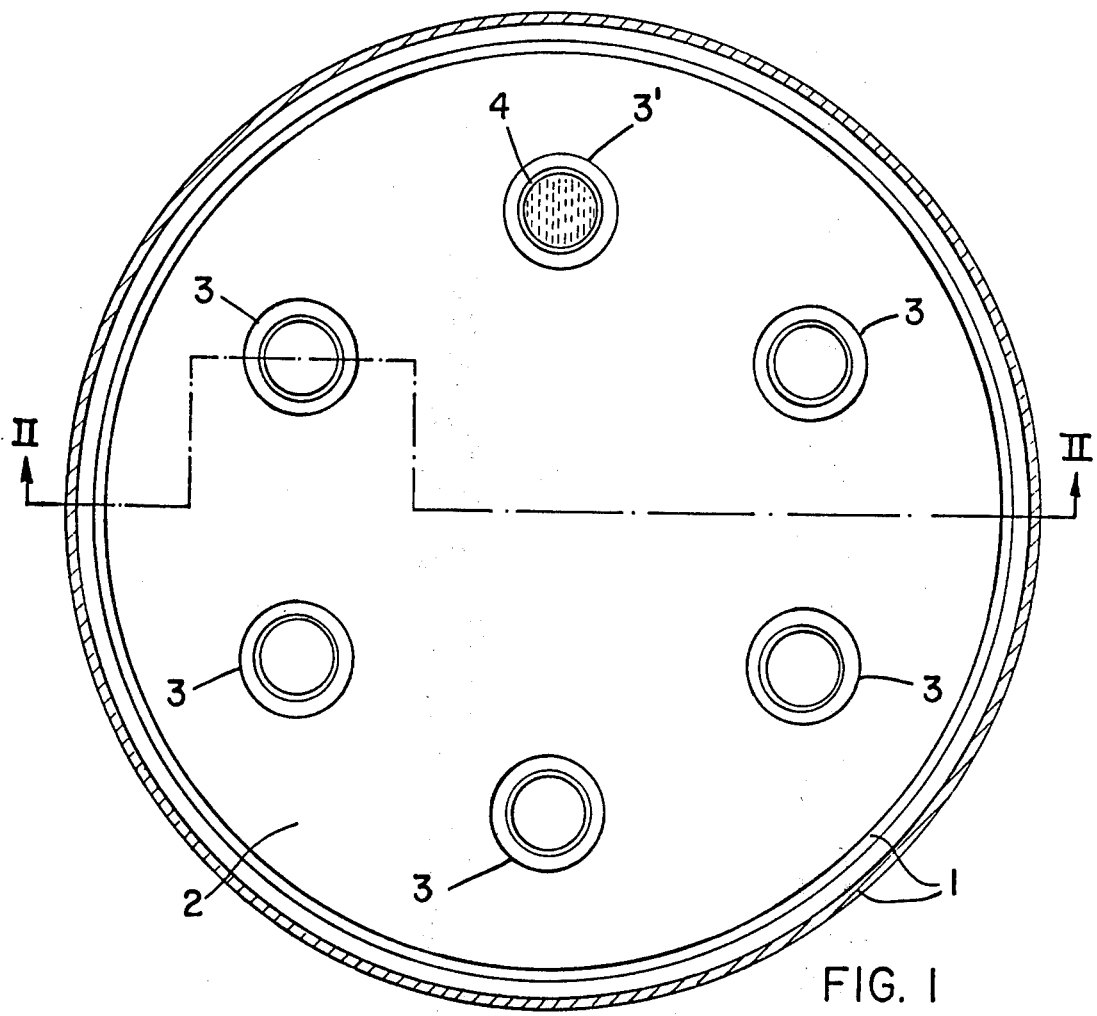
FIG. 1 shows a Petri dish containing substrate, seen from above and in section along the line I—I in FIG. 2, and provided with supporting elements according to the invention, for carrying out the experiments desired.
Figure 2:
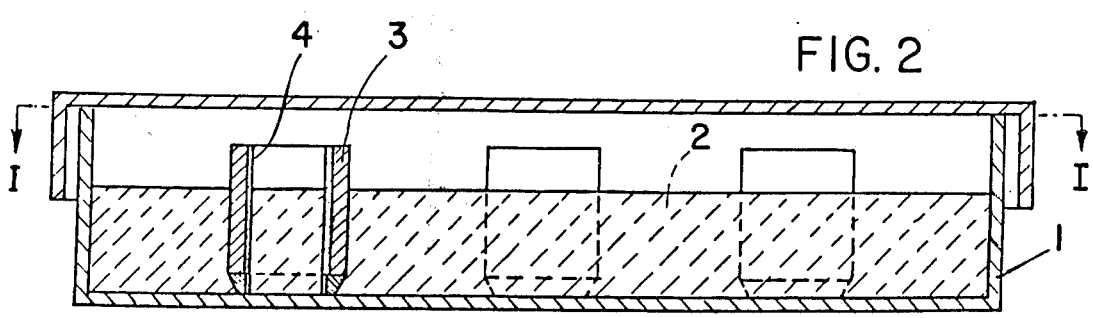
FIG. 2 is a view in cross-section along line II—II in FIG. 1.
Figure 3:
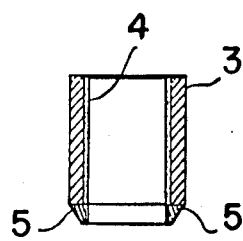
FIG. 3 is a vertical sectional view through one embodiment of a supporting element according to the invention.

The different sugars are added to a solid or semi-solid substrate, which is inoculated with the bacterium to be examined. The sugars are brought into contact with the substrate by means of a supporting element according to the invention, for example, of the form shown in FIG. 3. The supporting element 3 in this embodiment is tubular and has on the inside of the wall thereof a lining 4 containing a sugar (and an indicator if this is not contained in the substrate) to be used in the experiment. A ferromagnetic ring 5 is mounted at the bottom of the tubular supporting element. By means of one or more permanent-magnets or electromagnets, it is possible to draw the tubular supporting elements into position through the substrate in a Petri dish. This positioning is shown in FIGS. 1 and 2. Here, the Petri dish is indicated by numeral 1. The substrate which has been inoculated with the bacterium culture to be determined, is indicated at 2. Six tubular supporting elements of the type shown in FIG. 3 have been placed in the substrate. Each supporting element 3 has a lining 4 carrying its own type of sugar. This varies from one supporting element to the next in the substrate dish. The outcome of the fermentation reaction (which sugars, if any, are fermenting) is a diagnostic aid when determining the bacterium. Fermentation is revealed by a change in the indicator color. Such a change has been indicated in the substrate which is encompassed or confined by the supporting element designated at numeral 3' in FIG. 1. The fermentation causing the indicator to change color, is initiated after the various sugars and the indicator, if added to the bodies in the linings 4 of the six supporting elements have diffused into the substrate enclosed by each individual supporting element the diffusion of the sugar into the confined area producing an equilibrium concentration thereof in the confined area.

The lining 4 may, for example, be of paper or cellulose, and it rests, in this embodiment, on a step or shelf formed at the lower end of the tubular supporting element 3 by the ring 5.

Figure 4:
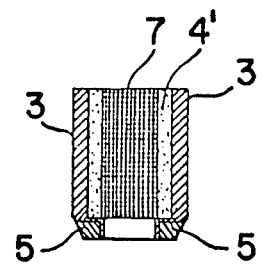
FIG. 4 is a vertical sectional view through another embodiment of the supporting element.
Figure 5:
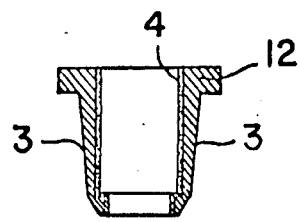
FIG. 5 is a vertical sectional view through another embodiment of the supporting element.
Figure 6:
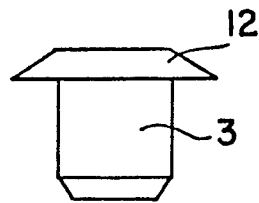
FIG. 6 is a side elevational view of another embodiment of the supporting element.
Figure 7:
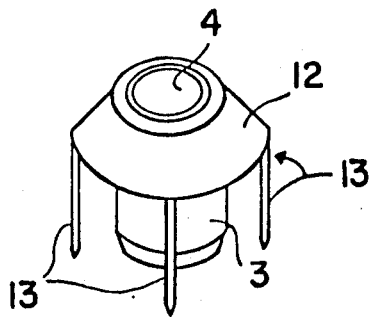
FIG. 7 is a top perspective view of another embodiment of the supporting element.
Figure 8:
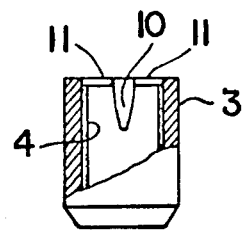
FIG. 8 is a side elevational view, partly broken away and in section, of another embodiment of the supporting element.
Figure 9:
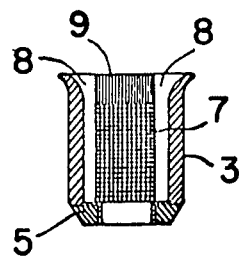
FIG. 9 is a vertical sectional view through another embodiment of the supporting element.
Figure 10:
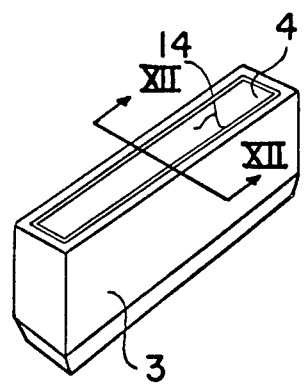
FIG. 10 is a top perspective view of another embodiment of the supporting element.
Figure 11:
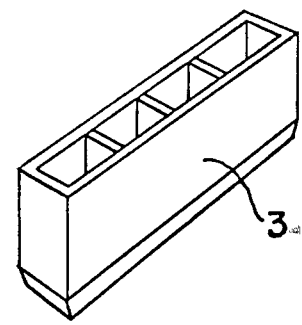
FIG. 11 is a top perspective view of another embodiment of the supporting element.
Figure 12:
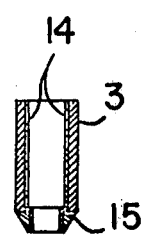
FIG. 12 is a section taken on line XII—XII in FIG. 10.
Figure 13:
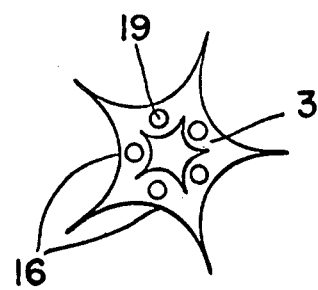
FIG. 13 is a top plan view of another embodiment of the supporting element.
Figure 14:
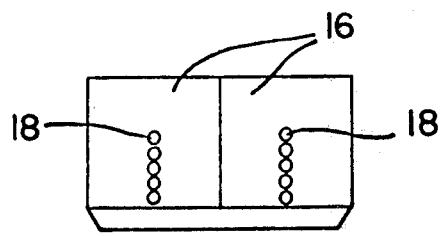
FIG. 14 is a side elevation view of the embodiment of of FIG. 13.
Figure 15:
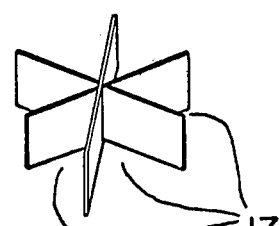
FIG. 15 is a top perspective view of another embodiment of the supporting element.

Instead of the lining, there may be provided a perforated wall lamella which forms the inner boundary of a cavity 4' in the wall of the tube 3a as shown in FIG. 4.

The sugar is placed in the cavity. It is placed there either in its original form or it is absorbed in a lining or mixed with an inert mass. It diffuses through the perforated lamella and into the substrate encompassed by the tubular supporting element when this is pressed into the inoculated substrate.

The tubular supporting elements may consist of various suitable materials, for example, a plastic. The material may contain ferromagnetic material, either inserted or cast in position, or the supporting elements may be made of a ferromagnetic material, such as steel.

If, in special cases, more powerful magnetic forces are required than those obtainable by the ferromagnetic ring 5 in FIG. 3, (even when adding additional ferromagnetic material into the wall of the tube) the tubular supporting element may, as indicated at **3*b* in FIG. 5, have a ferromagnetic collar 12 or other suitably shaped member disposed around the upper end of the tube. In FIG. 5 the entire wall of the tubular supporting element, including the collar, consists of a ferromagnetic material. The supporting element has, in this case, a somewhat tapered shape as compared to the one shown in FIG. 3. In FIG. 6 the ferromagnetic aollar 12' is of triangular cross-section disposed on a tubular supporting element 3*c* of the type shown, for example, in FIG. 3. Should it be necessary to make the supporting element more stable when it has a ferromagnetic collar at the upper end, the supporting element may be provided with four supporting legs 13 as shown in FIG. 7**.

The embodiment in FIG. 8 has a projectile-like body 10 placed centrally in the tubular supporting element 3. This projectile-like body is supported from element 3 by a spider 11. The body 10 may be provided, on its outer face, with a coating containing the active, diffusible substance corresponding to that in the lining 4. In this manner, diffusion equilibrium in the substrate mass is rapidly achieved.

Alternatively, different diffusible substances may be used in lining 4 and on the surface of the body 10.

The body 10 may be hollow and perforated. The diffusible material may then be placed in the body either during the the manufacturing process or at a later stage. The supporting elements intended for the latter purpose are manufactured without active materials in the bodies 10. These meet a demand in certain situations, for example, in certain experiments where the experimenter wishes himself to add the materials to be tested. This is achieved by allowing them to drip down into the hollow bodies.

The supporting element as shown in FIG. 9 is suitable for experimental purposes connected with the same requirements for use as indicated above. The diffusible, active substance is allowed to drip down from above, into cavity 8, at the funnel-shaped, widened part of the tubular supporting element 3. The substances diffuse into the substrate mass through a perforated inner part 7 of the supporting element, while a closed, upper part 9 prevents the substances from leaking out onto the surface of the substrate. In this way, the substances diffuse into the substrate along the wall of inner part 7.

The term "tubular supporting elements" here also refers to supporting elements which are not of circular cylindrical shape, and for example, the supporting elements may be in the form of an elongated box, as shown at 13 in FIG. 10. Such a shape is suitable if it is required to guide the diffusion in a particular direction. This is achieved by placing the prepared lining 4 on one of the short walls as indicated in the figure. The diffusion will then spread along the body 13 of the supporting element towards the opposite short wall. If the linings are placed along one long side or along both sides as indicated at 14, diffusion equilibrium will be rapidly established. As shown in FIG. 12, the rectangular supporting element in FIG. 10 has neither base nor cover, and the supporting element may carry a ferromagnetic material as shown at ring 15. Further, the supporting element may be provided with a roof or cover, if desired.

FIG. 11 shows a different embodiment of a supporting element **13*a* in the form of an elongated, rectangular structure, in which the interior space is divided by walls 20 into four equal spaces, each of which may have a lining containing a different substance. A section through FIG. 11 would have the same appearance as the one through FIG. 10 and shown in FIG. 12**.

In the embodiments shown, one of the objects of the invention is to keep the reaction confined to a certain area. According to the invention, the supporting elements may, however, also be so designed that only the first stage of the diffusion is controlled and guided in a particular direction, while the final stage is free and unrestricted. An example of this is shown in FIGS. 13 and 14. In this case, the supporting element 23 is provided on their outer surface with longitudinal concavities 16 having small holes 18. These lead into longitudinal passages 19. These passages may either be furnished with active substances during manufacture, or the substances to be used or investigated may be added during the experiment. This can be achieved by depositing drops of the substances into the longitudinal passages 19.

The substances will, in time, diffuse out into the substrate through the holes 18. As the diffusion spreads further outwards, the direction will be determined by the shape and size of the curved part. It is not until a later stage, when the dispersal has proceeded beyond the confining borders, that it becomes uncontrolled in all directions.

As explained with reference to FIGS. 4 and 9, the supporting element may also be made with a perforated wall lamella confining a chamber into which the substances of interest may be introduced. Alternatively, the supporting element may be without chambers and perforations in the walls. In such a case, the substances in question may be added in the form of, for example, a paste in the longitudinal concavities 16, or they may be contained in a lining which, in a suitable manner, is fixed to the outside of the supporting element.

The supporting element shown in FIG. 13 is hollow in the center. The supporting element may also be made without this cavity, but if so, it should be thin enough to ensure that it does not cause cracks to form in the surrounding substrate during or after its introduction.

In FIG. 15, a star-shaped supporting element is shown wherein a plurality of flat walls 19 intersect along a common line. This supporting element also causes the substances to be diffused according to a fixed pattern. The substances in question are placed — or have already been placed — in the angles 17 formed between adjacent walls 19.

The disclosed embodiments merely serve to illustrate the invention and not to limit it, inasmuch as variations and modifications will become apparent which will fall within the scope of the invention as defined in the appended claims.

What is claimed is:

1. For use in combination with a substrate containing an agent to carry out biological and chemical diffusion tests in microbiological, serological, immunological, clinical-chemical and similar laboratory work: a carrying body including a wall which is shaped to confine a substantially closed area on one side thereof when the wall is forced substantially to the bottom of the substrate, and means operatively associated with said body for diffusing an active substance from said body along the depth of penetration thereof into the confined area of the substrate for producing a substantial equilibrium concentration of the active substance in said confined area, the reactivity of the active substance and agent being the subject of the investigation, said body having shaped means on said wall of ferromagnetic material for the application of magnetic force thereto to urge the wall into said substrate.

2. The invention as claimed in claim 1 wherein said carrying body is formed as an annulus thereby to define a closed cross-sectional area, said shaped means comprising an annular collar.

3. The invention as claimed in claim 2 comprising stabilizing legs extending downwardly with respect to said annular collar.

4. The invention as claimed in claim 2 wherein said shaped means is of triangular cross-section.